United States Patent
Kuramori et al.

(10) Patent No.: US 7,532,925 B2
(45) Date of Patent: *May 12, 2009

(54) APPARATUS AND METHOD OF EVALUATING DEGREE OF WORK COMFORT

(75) Inventors: Akira Kuramori, Kanagawa (JP); Noritaka Koguchi, Kanagawa (JP); Masayoshi Kamijo, Nagano (JP); Tsugutake Sadoyama, Ibaraki (JP); Satoshi Hosoya, Nagano (JP); Yoshio Shimizu, Nagano (JP)

(73) Assignee: The Yokohama Rubber Co., Ltd., Tokyo (JP)

( * ) Notice: Subject to any disclaimer, the term of this patent is extended or adjusted under 35 U.S.C. 154(b) by 478 days.

This patent is subject to a terminal disclaimer.

(21) Appl. No.: 10/522,023
(22) PCT Filed: Jul. 18, 2003
(86) PCT No.: PCT/JP03/09154
§ 371 (c)(1), (2), (4) Date: Jan. 21, 2005
(87) PCT Pub. No.: WO2004/008957
PCT Pub. Date: Jan. 29, 2004

(65) Prior Publication Data
US 2005/0277843 A1 Dec. 15, 2005

(51) Int. Cl.
A61B 5/04 (2006.01)
G08B 23/00 (2006.01)
(52) U.S. Cl. ...................... 600/546; 340/576
(58) Field of Classification Search ................ 600/546, 600/590; 340/576, 573.1; 73/379.01, 379.02, 73/865.1
See application file for complete search history.

(56) References Cited

U.S. PATENT DOCUMENTS 4,344,441 A   8/1982  Radke
4,667,513 A * 5/1987  Konno .................. 600/546
5,195,531 A   3/1993  Bennett (Continued)

FOREIGN PATENT DOCUMENTS

JP      57-043730 A1   3/1982

(Continued)

OTHER PUBLICATIONS

Kuramori, Akira, et al. Amendment to the claims in U.S. Appl. No. 10/942,045. Feb. 14, 2007.*

(Continued)

Primary Examiner—Max Hindenburg
Assistant Examiner—John Pani
(74) Attorney, Agent, or Firm—Knobbe Martens Olson & Bear, LLP.

(57) ABSTRACT

An apparatus and method for evaluating the degree of work comfort of a user is disclosed. A pair of sensors detect myoelectric potentials of a pair of bilaterally symmetrical muscles. A waveform processing unit generates a synchronous contraction waveform by either using the smaller value between signals from the two muscles at a given time, or by determining the geometric mean between the signals at a given time. An evaluation unit uses the intensity or frequency information from the synchronous contraction waveform to evaluate the user's level of comfort performing a task such as driving.

18 Claims, 4 Drawing Sheets

U.S. PATENT DOCUMENTS 6,233,472 B1    5/2001    Bennett et al.

FOREIGN PATENT DOCUMENTS

| JP | 2002-214083 | A1 |   | 7/2002 |
|---|---|---|---|---|
| JP | 2002230699 | A | * | 8/2002 |
| JP | 2003-177079 | A1 |   | 6/2003 |

OTHER PUBLICATIONS

Okamoto, Nobuhisa, et al. "Driving load decision device, driving load decision method, computer program for implementing said method, and storage medium in which said computer program is stored." English translation of JP-2002230699 by Schreiber Translations, Inc. May 2007.*

Lehman, Gregory, et al. "The importance of normalization in the interpretation of surface electromyography: A proof of principle." Sep. 1999. Journal of Manipulative and Physiological Therapeutics. vol. 22, No. 7. pp. 444-446.*

Tanaka, Jun et al. "Workload of using a driver assistance system". Oct. 2000. IEEE Intelligent Transportation Systems Conference Proceedings. pp. 382-386.*

International Search Report for PCT/JP03/09154 mailed on Sep. 2, 2003.

Manabu Yoshikawa et al., "Sokoji ni Okeru Untensha no Shinshin Han'no no Keisoku", Dai 11 Kai Sinshu Chiku Keisoku Seigyo Kenkyu Koenkai Koen Ronbunshu, Keisoku Jido Seigyo Gakkai Chubu Shibu Shinshu Chiku Keisoku Seigyo Kenkyu Iinkai, 1998, pp. 1-4.

Healey, Jennifer A. "Wearable and automotive systems for affect recognition from physiology." May 2000. Massachusetts Institute of Technology. All, particularly pp. 93-126.

Office Action dated Jul. 9, 2007 from co-pending U.S. Appl. No. 10/522,022, filed Jan. 21, 2005.

* cited by examiner

| COMPARISON PAIR | S_a | L_1 | L_2 | L_3 | L_4 | S_b | L_5 | L_6 | L_7 | L_8 | S_c |
|---|---|---|---|---|---|---|---|---|---|---|---|
| NS-OS | | < | | < | | | | | < | | |
| NS-US | | < | | | < | | | | < | | |
| OS-US | | | | > | | | | > | | | |

(5% SIGNIFICANT LEVEL)

APPARATUS AND METHOD OF EVALUATING DEGREE OF WORK COMFORT

TECHNICAL FIELD

The present invention relates to an apparatus and method of evaluating a degree of work comfort by measuring a myoelectric potential during a work activity which is performed antagonistically by a pair of left and right muscles (carnes) provided in a human body in bilaterally symmetrical relation and, more particularly, to an apparatus and method of evaluating a degree of comfort of, e.g., wheel steering when a driver steers a vehicle wheel.

BACKGROUND ART

To provide a vehicle such as an automobile and a tire which allow comfort wheel steering, automobile makers and tire makers in these days have investigated the wheel steering comfort of a vehicle and performed the development of vehicles and tires by using various methods.

In the development of vehicles and tires, when it is evaluated whether or not the steering of a wheel is comfort, the evaluation is generally performed in most cases by using subjective Judgment by a driver or quantitatively measuring the behavior of a vehicle by providing the vehicle with a measurement sensor for an acceleration rate or the like and acquiring physical measurement data representing the behavior of the vehicle.

To evaluate the degree of load placed by a given work activity while it is performed, it has also been performed in these days to acquire an electromyogram representing the waveform of a myoelectric potential from an activity worker and thereby quantitatively recognize the load on the muscle of the activity worker. It is considered that the myoelectric potential enables proper evaluation of the degree of load placed by a given work activity while it is performed since the myoelectric potential can be measured easily and conveniently and is also high in responsivity. It can also be considered to apply a method of evaluating a degree of load placed by a work activity which uses the electromyogram to the steering of a vehicle wheel by a driver.

However, since the steering of the vehicle wheel by the driver is a work activity which is performed antagonistically by deltoid muscles which are a pair of left and right muscles provided in a human body in bilaterally symmetrical relation, the fact is that the one of the muscles on which less load is placed does not correspond to a higher degree of comfort during wheel steering.

For example, when a force for wheel steering is small, the load on the muscles of the drive is reduced but the problem is encountered that the steering wheel should be held incessantly with the small force. When the force for wheel steering is large, the load on the muscles when the driver steers the wheel is increased but the necessity to constantly hold the steering wheel is reduced because the wheel is stable.

Accordingly, the degree of comfort of wheel steering cannot be evaluated properly from an index of load on a muscle obtained through the measurement of an electromyogram.

There is also a method which measures the fluctuations of the electroencephalogram, the fluctuations of the heart rate, the blood pressure, and the like as the bio-information of the driver. In either case, however, it is necessary to give a specified restriction to the driver, such as the retention of constant breathing, so a problem of placing extra burden on the driver is encountered. In addition, such bio-information has a problem in that it requires a sufficiently long measurement period in terms of analysis performed as a post process and a result which is high in responsivity cannot be obtained. Accordingly, the degree of comfort of actual wheel steering cannot be evaluated properly.

Such problems are not limited to the steering of a vehicle wheel and similarly occur in the case where the degree of work comfort is evaluated when a pair of left and right muscles provided in a human body in bilaterally symmetrical relation antagonistically perform a work activity.

In view of the foregoing, it is therefore an object of the present invention to provide an apparatus for evaluating a degree of work comfort by measuring a myogenic action during a work activity which is performed antagonistically by a pair of left and right muscles provided in a human body in bilaterally symmetrical configuration and provide an apparatus and method of evaluating a degree of work comfort which allow the evaluation of the degree of comfort of a work activity from the result of short-period measurement without imposing a restriction on an activity worker.

DISCLOSURE OF THE INVENTION

According to the present invention, there is provided an apparatus for evaluating a degree of work comfort by measuring myoelectric potentials during a work activity which is performed antagonistically by a pair of left and right muscles provided in a human body in bilaterally symmetrical relation, the apparatus including:

a pair of detection sensors for detecting the myoelectric potentials produced by actions of the pair of left and right muscles provided in the human body in bilaterally symmetrical relation during the work activity;

an amplifier for amplifying the pair of myoelectric potentials detected by the detection sensors;

a waveform Processing unit for generating a synchronous contraction waveform of the pair of muscles from time-series waveforms of the pair of amplified myoelectric potentials; and an evaluation unit for evaluating a level of the degree of comfort of the work activity from intensity information of the generated synchronous contraction waveform or from frequency information of the generated synchronous contraction waveform of the generated synchronous contraction waveform contained in a specified intensity range.

At this time, it is preferable that the evaluation unit calculates the intensity information of the generated synchronous contraction waveform or the frequency information of the generated synchronous contraction waveform at specified time intervals and evaluates the level of the degree of comfort of the work activity at the specified time intervals based on results of the calculation.

Further, it is preferable that the waveform processing unit performs full-wave rectification with respect to the time-series waveforms of the pair of myoelectric potentials and designates the smaller one of respective values at the same time of the time-series waveforms of the pair of myoelectric potentials that have been subjected to the full-wave rectification as a signal value of the synchronous contraction waveform. In this case, it is preferable that the waveform processing unit performs a normalizing process with respect to the time-series waveforms of the pair of amplified myoelectric potentials by using a maximum myoelectric potential and generate the synchronous contraction waveform by using the time-series waveforms that have been subjected to the process.

Alternatively, it is also preferable that the waveform processing unit performs full-wave rectification with respect to the time-series waveforms of the pair of myoelectric potentials and designates a geometric mean value of signal values at the same time of the time-series waveforms of the pair of myoelectric potentials that have been subjected to the full-wave rectification as a signal value of the synchronous contraction waveform.

The work activity is exemplified by steering of a wheel in driving a vehicle.

The pair of muscles are exemplified by deltoid muscles positioned in shoulders of the human body.

Further, according to the present invention, there is provided a method of evaluating a degree of work comfort by measuring myoelectric potentials during a work activity which is performed antagonistically by a pair of left and right muscles provided in a human body in bilaterally symmetrical relation, the method including:

a step of detecting the myoelectric potentials produced by actions of the pair of left and right muscles provided in the human body in bilaterally symmetrical relation during the work activity and amplifying the pair of myoelectric potentials;

a step of generating a synchronous contraction waveform of the pair of muscles from time-series waveforms of the pair of amplified myoelectric potentials; and a step of evaluating a level of the degree of comfort of the work activity from intensity information of the generated synchronous contraction waveform or from frequency information of the generated synchronous contraction waveform contained in a specified intensity range.

At this time, it is preferable that the step of evaluating the level of the degree of comfort of the work activity includes calculating the intensity information of the generated synchronous contraction waveform or the frequency information of the generated synchronous contraction waveform at specified time intervals and evaluating the level of the degree of comfort of the work activity at the specified time intervals based on results of the calculation.

Here, it is preferable that the step of generating the synchronous contraction waveform includes performing full-wave rectification with respect to the time-series waveforms of the pair of myoelectric potentials and designating the smaller one of respective values at the same time of the time-series waveforms of the pair of myoelectric potentials that have been subjected to the full-wave rectification as a signal value of the synchronous contraction waveform. At this time, it is preferable that, in the step of generating the synchronous contraction waveform, the waveform processing unit performs a normalizing process with respect to the time-series waveforms of the pair of amplified myoelectric potentials by using a maximum myoelectric potential and generate the synchronous contraction waveform by using the time-series waveforms that have been subjected to the process.

Alternatively, it is also preferable that the step of generating the synchronous contraction waveform includes performing full-wave rectification with respect to the time-series waveforms of the pair of myoelectric potentials and designating a geometric mean value of signal values at the same time of the time-series waveforms of the pair of myoelectric potentials that have been subjected to the full-wave rectification as a signal value of the synchronous contraction waveform.

The work activity is exemplified by steering of a wheel in driving a vehicle. The pair of muscles are exemplified by deltoid muscles positioned in shoulders of the human body.

BEST MODE FOR CARRYING OUT THE INVENTION

A detailed description will be given herein below to an apparatus for evaluating a degree of work comfort according to the present invention based on a preferred embodiment shown in the accompanying drawings.

Figure 1:
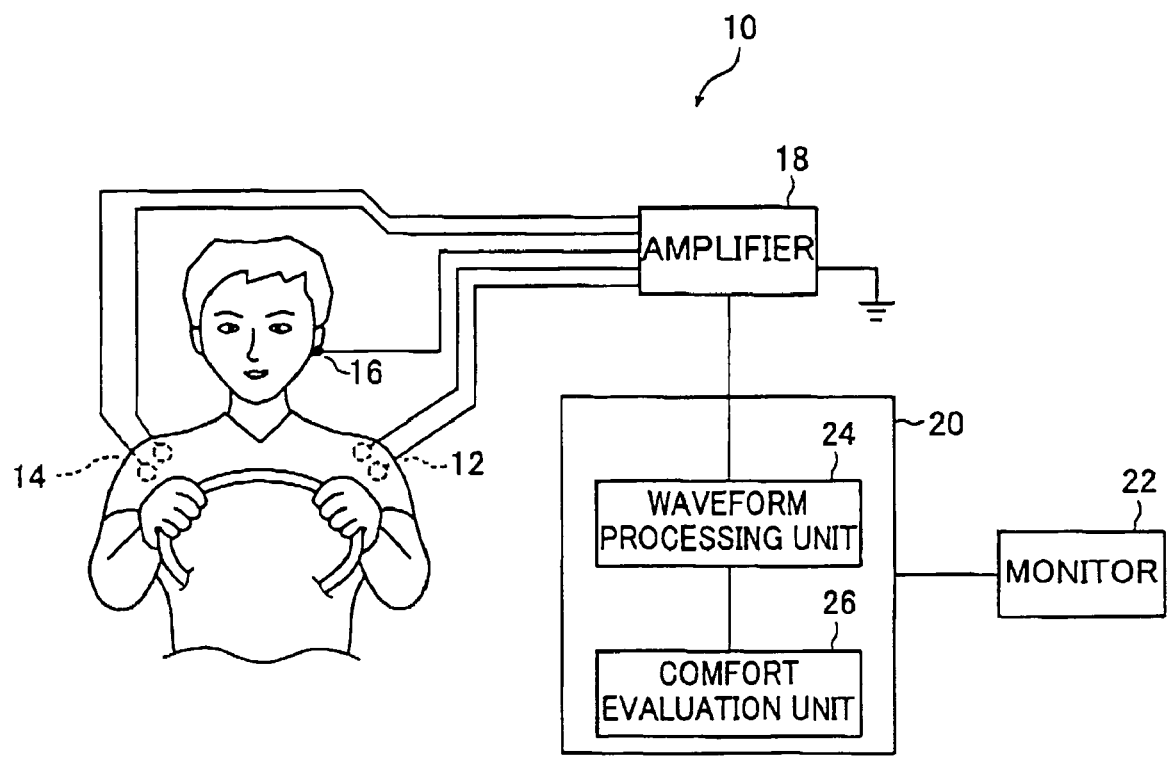
FIG. 1 is a schematic structural view showing a structure of a steering comfort evaluating apparatus as an example of an apparatus for evaluating a degree of work comfort according to the present invention.

FIG. 1 is a schematic structural view of a steering comfort evaluating apparatus 10 obtained by applying the apparatus for evaluating a degree of work comfort according to the present invention to the wheel steering operation of a driver.

The steering comfort evaluating apparatus 10 is an apparatus for evaluating a degree of comfort of wheel steering by a driver who is driving a vehicle and is comprised of detection sensors 12 and 14 for detecting myoelectric potentials at the left and right deltoid muscles of the driver, an electrode 16, an amplifier 18 for amplifying the myoelectric potentials from the detection sensors 12 and 14, a processing unit 20 for evaluating the degree of comfort of wheel steering from the time-series waveforms of the amplified myoelectric potentials of the left and right deltoid muscles, and a monitor 22 for monitor displaying the result of evaluation.

The detection sensor 12 is a sensor for detecting a myoelectric potential at the left deltoid muscle of the driver and is composed of a pair of skin surface electrodes (e.g., Ag/AgCl plate-like electrodes, Ag electrodes, or stainless steel electrodes). The pair of skin surface electrodes are attached to the surface of the left shoulder in which the deltoid muscle is positioned in spaced apart relation each other at a given distance, e.g., 2 cm.

The detection sensor 14 is a sensor for detecting a myoelectric potential at the right deltoid muscle of the driver and is composed of a pair of skin surface electrodes, similarly to the detection sensor 12. The pair of skin surface electrodes are attached to the surface of the right shoulder in which the deltoid muscle is positioned in spaced apart relation each other at a given distance, e.g., 2 cm.

Figure 2:
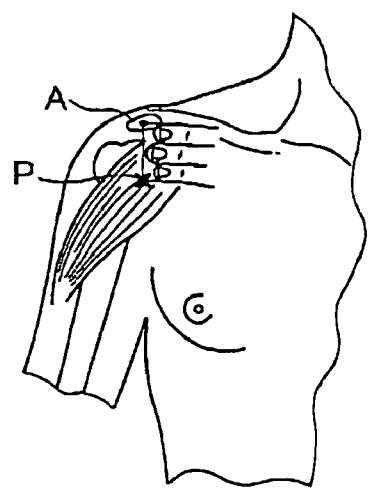
FIG. 2 is a view illustrating deltoid muscles at which myoelectric potentials are measured in the steering comfort evaluating apparatus shown in FIG. 1.

The attachment of the detection sensors to the surface of the skin of the driver is performed by rubbing the skin surface by using a scrub, removing contamination therefrom by using alcohol, and using an electrode glue. At this time, contamination is removed until electric resistance reaches a value of 30 kΩ or less (preferably, 5 kΩ). The two electrodes are attached to the bellies of the muscles to be measured in parallel relation to the muscle fibers. The positions of attachment are determined to avoid innervative areas so that, as shown in FIG. 2, each of the two electrodes is attached to the position P spaced apart in a longitudinal direction of the arm from the edge portion A of the acromion by the widths of three fingers to have a given distance therebetween.

On the other hand, the electrode 16 is an earth electrode attached to the earlobe of the driver, which is an electrically inactive position, to maintain the potential of the driver constant. The electrode 16 is provided to perform precise measurement using the detection sensors 12 and 14. The electrode 16 connected to the amplifier 18 is earthed via the amplifier 18.

The amplifier 18 is a well-known operational amplifier for amplifying the myoelectric potentials detected by the detection sensors 12 and 14.

The myoelectric potentials detected by the detection sensors 12 and 14 and amplified are sent to the processing unit 20.

The processing unit 20 is comprised of a waveform processing unit 24 and a comfort evaluation unit 26.

The processing unit 20 is a unit composed of a computer, while the waveform processing unit 24 and the comfort evaluation unit 26 are constituted to perform individual functions by executing programs.

Each of the waveform processing unit 24 and the comfort evaluation unit 26 may also be composed of a dedicated circuit.

The waveform processing unit 24 is a portion which samples the time-series waveforms of the myoelectric potentials, performs full-wave rectification, and then normalizes each of the time-series waveforms of the myoelectric potentials by using a maximum myoelectric potential preliminarily measured by using the detection sensors 12 and 14 and recorded/held to calculate an index (Index), while outputting, as a synchronous contraction waveform, a waveform generated by selecting the smaller one of the values of indices at the same time calculated by normalizing the myoelectric potentials of the pair of left and right deltoid muscles. The synchronous contraction waveform will be described later.

The maximum myoelectric potential used herein is a myoelectric potential when the driver places maximum load on the deltoid muscles to cause a muscle action. The measurement of the maximum myoelectric potential is performed every time the detection sensors 12 and 14 are attached. The reason for normalizing each of the time-series waveforms of the myoelectric potentials by using the maximum myoelectric potential is that the electric resistance of each of the detection sensors 12 and 14 slightly changes every time the detection sensors 12 and 14 are attached and the magnitudes of the detected myoelectric potentials change accordingly.

The waveform processing unit 24 may also be constituted to generate a synchronous contraction waveform which uses a geometric mean value of the signal values of the pair of myoelectric potentials at the left and right deltoid muscles as a signal value. In this case, it is unnecessary to make an adjustment by normalizing each of the time-series waveforms of the left and right myoelectric potentials by using the maximum myoelectric potential so that the measurement of the maximum myoelectric potential is not required.

The comfort evaluation unit 26 is a portion which calculates intensity information from the synchronous contraction waveform generated in the waveform processing unit 24 at specified time intervals and evaluates the level of the degree of comfort of wheel steering by the driver from the result of the calculation.

The intensity information of the synchronous contraction waveform indicates herein, e.g., the RMS (root means square) value (effective value) or integral value of the synchronous contraction waveform which is calculated at intervals of, e.g., 0.1 to 0.5 seconds, an integral value of the envelope of the synchronous contraction waveform, or the like.

Instead of calculating the intensity information of the synchronous contraction waveform, it is also possible to calculate the frequency information of the synchronous contraction waveform and evaluate the degree of comfort of wheel steering based on the frequency information. The frequency information of the synchronous contraction waveform indicates, e.g., the probability or number of times of the signal value of the synchronous contraction waveform which falls within a specified range of RMS values or the like.

The comfort evaluation unit 26 evaluates the level of the degree of comfort of wheel steering by the driver by, e.g., comparing the RMS value of the synchronous contraction waveform with the set value of each of levels that has been predetermined for the level classification of the degrees of comfort of wheel steering by the driver. Alternatively, the comfort evaluation unit 26 evaluates the level of the degree of comfort of wheel steering by the driver by, e.g., comparing the frequency information of the synchronous contraction waveform with the set probability of each of levels that has been predetermined for the level classification of the degrees of comfort of wheel steering by the driver.

Such a result of evaluation is sent to the monitor 22 together with the synchronous contraction waveforms and the time-series waveforms of the myoelectric potentials of the left and right deltoid muscles to be displayed thereon.

Thus, the steering comfort evaluating apparatus 10 is characterized in that it generates the synchronous contraction waveform from the time-series waveforms of the myoelectric potentials at the left and right deltoid muscles and evaluates the degree of comfort of wheel steering by the driver by using the intensity information or frequency information of the synchronous contraction waveform.

In general, the steering of a wheel by a driver is performed by the action of steering a vehicle wheel (steer). In the case of turning the vehicle to the right, e.g., the steering of the wheel involves the upward movement of the left hand holding the steering wheel so that the deltoid muscle in the left shoulder of the driver is contracted. On the other hand, the right hand only performs a helping function by touching the wheel so that the deltoid muscle in the right shoulder of the driver is slackened. In the case of turning the vehicle to the left, the deltoid muscle in the left shoulder of the driver is slackened, while the deltoid muscle in the right shoulder of the driver is contracted. The wheel steering by the driver which is performed by thus contracting one of the pair of left and right deltoid muscles provided in a human body in bilaterally symmetrical relation and slackening the other of the pair of deltoid muscles corresponds to a work activity which is performed antagonistically by a pair of left and right muscles provided in the human body in bilaterally symmetrical relation according to the present invention.

However, when extra tension is placed on the hands of the driver gripping the wheel due to any mental load or the like or when the driver tenses up because the steering of the wheel is difficult, the pair of left and right deltoid muscles are contracted in synchronism even during the steering of the wheel which is performed antagonistically by the pair of left and right deltoid muscles. The waveform of the myoelectric potential measured at this time is referred to as a synchronous contraction waveform.

Through such contraction of the deltoid muscles, the driver can obtain a force to hold the steering wheel. However, the force to hold the steering wheel in this case is information which cannot be obtained in the form of physical measurement data representing the behavior of the vehicle, such as an acceleration rate, by providing a measurement sensor such as a load cell.

The inventors of the present invention have found that the ease of wheel steering and the ease of control through wheel steering can be evaluated based on the intensity or frequency of the synchronous contraction and achieved the present invention.

Figure 3:
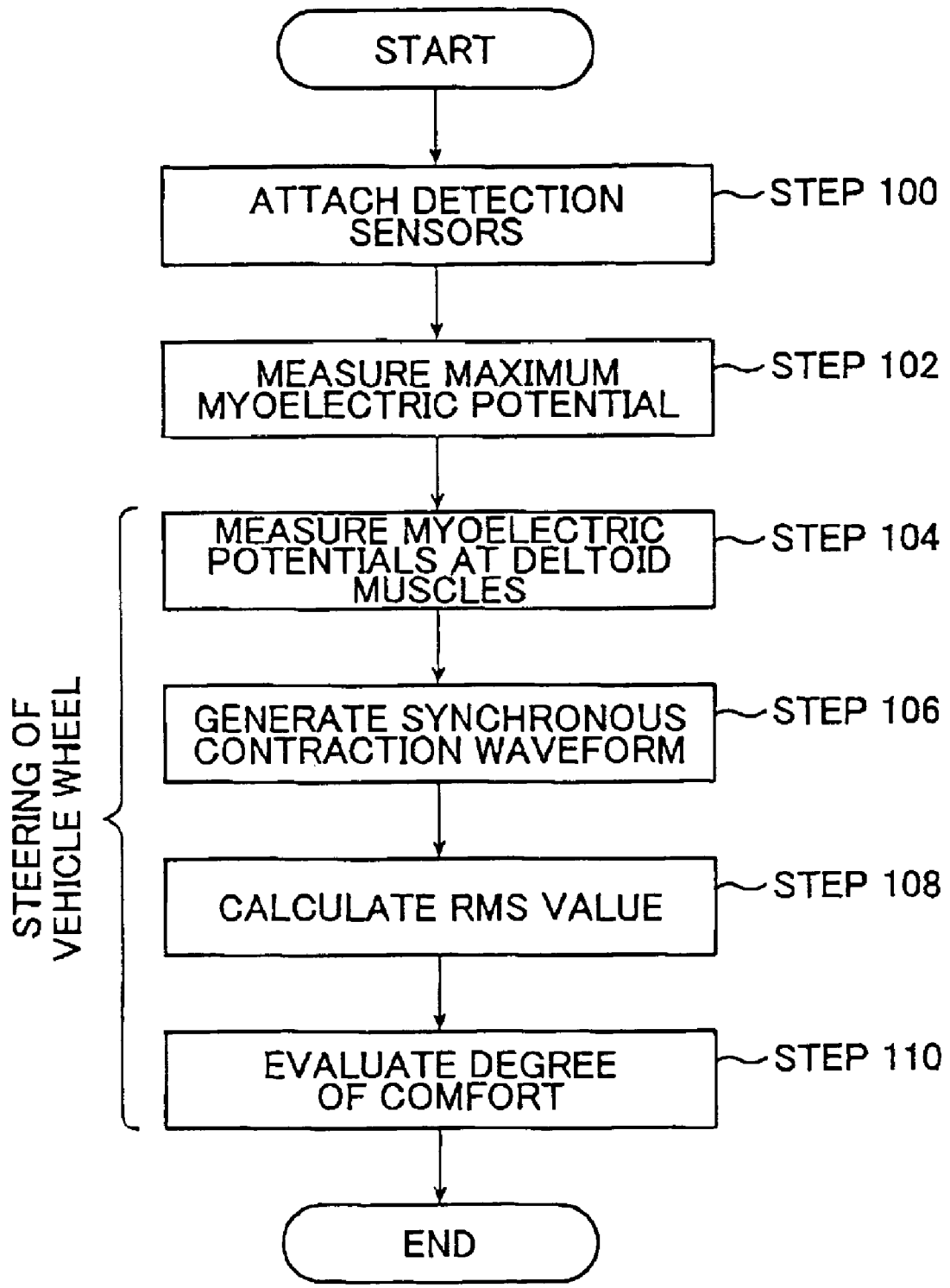
FIG. 3 is a flow chart showing a flow of an example of a method of evaluating a degree of work comfort according to the present invention.

In the case of evaluating the degree of comfort of wheel steering by using such a steering comfort evaluating apparatus 10, the detection sensors 12 and 14 are attached initially to the surfaces of the right and left shoulders in which the deltoid muscles are positioned, as shown in FIG. 3 (Step 100). At the same time, the electrode 16 is attached to the earlobe.

After the detection sensors 12 and 14 are attached, the maximum myoelectric potential when the driver maximally contracts both the left and right deltoid muscles is measured (Step 102). The maximum myoelectric potential is sent to the waveform processing unit 24 via the amplifier 18 and recorded/held therein. As a result, it becomes possible to normalize each of the myoelectric potentials measured thereafter and hold the myoelectric potential information constant which, otherwise, varies every time the detection sensors 12 and 14 are attached.

Then, the driving of the vehicle by the driver is initiated, the wheel steering by the driver is performed, and the myoelectric potentials of the left and right deltoid muscles of the driver are measured constantly (Step 104).

In the measurement of the myoelectric potentials, the myoelectric potentials are amplified by the amplifier 18 and then supplied to the waveform processing unit 24.

In the waveform processing unit 24, each of the time-series waveforms of the myoelectric potentials of the left and right deltoid muscles is subjected to full-wave rectification such that a signal waveform in which each value is not less than 0 is generated. Thereafter, each of the time-series waveforms of the myoelectric potentials that have been subjected to the full-wave rectification is normalized by using the maximum myoelectric potential that has been recorded/held. Further, the smaller one of the two values of the time-series waveforms at the same time that have been subjected to full-wave rectification is designated as the signal value of the synchronous contraction waveform, whereby the synchronous contraction waveform is generated (Step 106). By thus selecting information on the myoelectric potential produced in that one of the deltoid muscles which is closer to the slackened state in the work activity of wheel steering performed antagonistically by the pair of deltoid muscles, information on the myoelectric potential when the deltoid muscles are contracted in synchronism can be obtained.

In the comfort evaluation unit 26, the RMS values of the generated synchronous contraction waveform are calculated one after another at specified time intervals of, e.g., 0.1 to 0.5 seconds (step 108) and compared with the set value of each of the levels predetermined for the level classification of the degrees of comfort, whereby the degrees of comfort in the wheel steering by the driver are evaluated one after another (Step 110).

By thus measuring myoelectric potentials during the steering of a wheel which is performed antagonistically by a pair of left and right deltoid muscles provided in a human body in bilaterally symmetrical relation, the degree of comfort of wheel steering by the driver which varies from moment to moment during wheel steering is evaluated from the result of short-period measurement without imposing a restriction on the driver.

Figure 4:
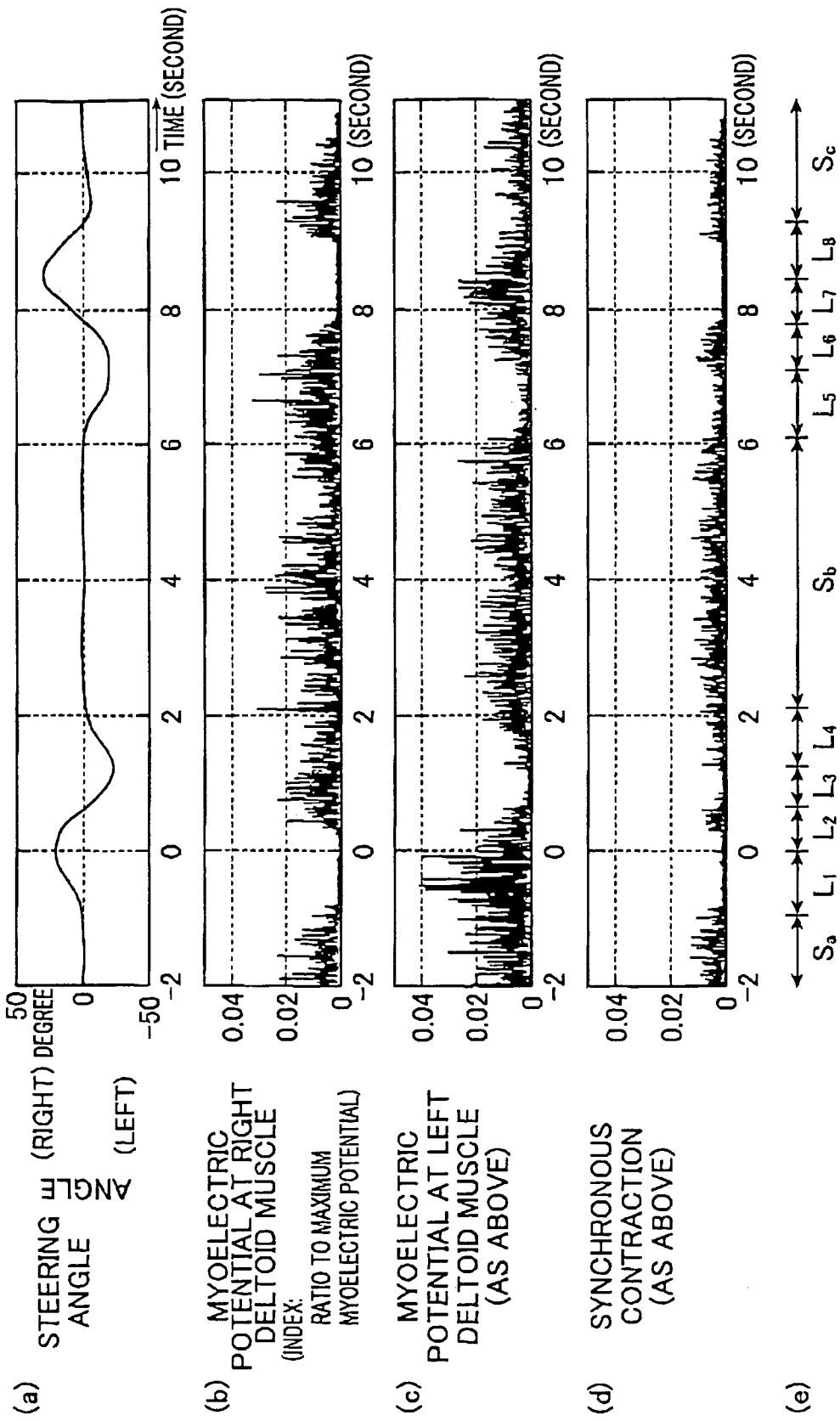
FIGS. 4(a) to 4(d) are views each showing an example of a time-series waveform obtained in the steering comfort evaluating apparatus shown in FIG. 1
FIG. 4(e) is a view illustrating regions obtained by dividing the time-series waveform shown in each of FIGS. 4(a) to 4(d)

FIGS. 4(a) to 4(d) show examples of various time waveforms when the method described above is implemented. FIG. 4(a) shows an example of the time-series waveform of the angle of wheel steering performed by the driver. FIGS. 4(b) and 4(c) show an example of the index (Index) obtained by calculating the ratio between the time-series waveforms of the myoelectric potentials at both the left and right deltoid muscles of the driver when the wheel steering shown in FIG. 4(a) is performed, which has been subjected to full-wave rectification. FIG. 4(d) shows an example of a synchronous contraction waveform (Index) generated from the time-series waveforms of the myoelectric potentials shown in FIGS. 4(b) and 4(c).

In this case, as can be seen from the time-series waveform of the steering angle shown in FIG. 4(a), the driver performed the steering of the wheel for a lane change at a maximum steering angle of about 20 to 30 degrees twice.

In FIG. 4(a), a positive steering angle indicates a state in which the wheel is steered to the right and a negative steering angle indicates a state in which the wheel is steered to the left. In the case of steering the wheel to the right, therefore, the contraction of the left deltoid muscle is significant as shown in FIG. 4(c). By contrast, a myoelectric potential is barely produced in the right deltoid muscle as shown in FIG. 4(b), which indicates that the right deltoid muscle is in a slackened state or in a state close to the slackened state.

In the case of turning to the right, therefore, a portion corresponding to the right turn in the waveform shown in FIG. 4(b) is generally selected as the synchronous contraction waveform. Likewise, a portion corresponding to the left turn in the waveform shown in FIG. 4(c) is generally selected in the case of turning to the left.

From the generated synchronous contraction waveform shown in FIG. 4(d), the RMS values of the waveform are calculated one after another at specified time intervals and compared with the set value of each of the levels predetermined for the level classification of the degrees of comfort of the wheel steering by the driver, whereby the degree of comfort of the wheel steering by the driver is evaluated.

Figures 5, 6:
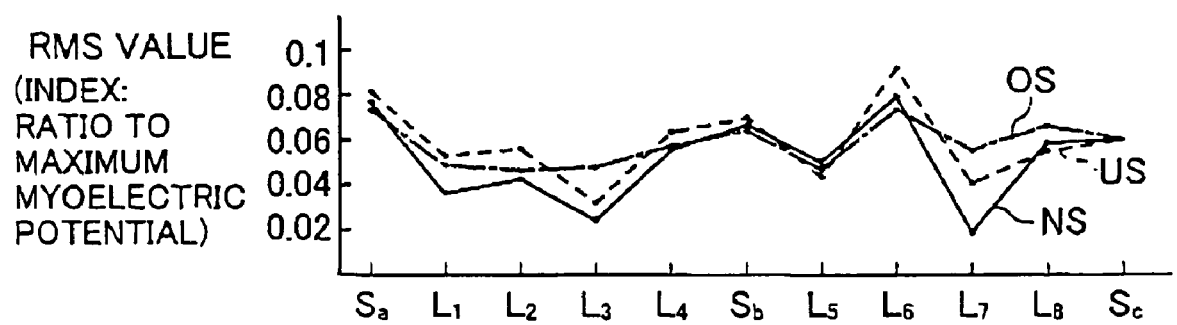
FIG. 5 is a view showing an example of the fluctuation of the RMS values of synchronous contraction waveforms obtained in the steering comfort evaluating apparatus shown in FIG. 1.
FIG. 6 is a view illustrating an example of the result of analyzing the distributions of the RMS values of the synchronous contraction waveforms obtained in the steering comfort evaluating apparatus shown in FIG. 1.

FIG. 5 shows the result of calculating the RMS values of the synchronous contraction waveforms acquired under the three conditions of US (Under-Steer), OS (Over-Steer), and NS (Neutral-Steer) that have been set as the turning characteristics of a vehicle. As shown in FIG. 4(e), the RMS values of the synchronous contraction waveforms acquired under the individual conditions were calculated in a divided manner in correspondence to the steering angles.

The region $S_a$ is a region where the steering angle is 0. The region $L_1$ is a region where the steering angle is positive and increases with time. The region $L_2$ is a region where the steering angle is positive and decreases with time. The region $L_3$ is a region where the steering angle is negative and the absolute value thereof increases with time. The region $L_4$ is a region where the steering angle is negative and the absolute value thereof decreases with time. The region $S_b$ is a region where the steering angle is 0. The region $L_5$ is a region where the steering angle is negative and the absolute value thereof increases with time. The region $L_6$ is a region where the steering angle is negative and the absolute value thereof decreases with time. The region $L_7$ is a region where the steering angle is positive and increases with time. The region $L_8$ is a region where the steering angle is positive and decreases with time. The region $S_c$ is a region where the steering angle is 0.

The RMS values in the individual regions were calculated by repeating the steering of the wheel shown in FIG. 4(a) five times under each of the US, OS, and NS conditions and subjected to the analysis of variance so that it was examined whether or not the RMS values had statistically significant differences among the US, OS, and NS.

On the other hand, the driver who performed the steering of the wheel was requested to perform subjective judgement on the degree of wheel steering. According to the result of the judgement, the steering of the wheel was performed most comfortably under the NS and next most comfortably under the US.

The US is one of the turning properties of a vehicle with which, when the vehicle in the state of running along an arcuate configuration while maintaining a given steering angle increases the driving speed thereof, the running of the vehicle expands outwardly from the above-mentioned arcuate configuration so that the turning radius is increased.

The OS is one of the turning properties of the vehicle with which, when the vehicle in the state of running along an arcuate configuration while maintaining a given steering angle increases the driving speed thereof, the running of the vehicle moves inwardly from the above-mentioned arcuate configuration so that the turning radius is reduced.

The NS is one of the turning properties of the vehicle with which, even when the vehicle in the state of running along an arcuate configuration while maintaining a given steering angle increases the driving speed thereof, the running of the vehicle does not deviate from the above-mentioned arcuate configuration so that the turning radius remains unchanged.

FIG. 5 shows the average value of the RMS (Index) values in the regions $S_a$, $L_1$, $L_2$, ..., and $S_c$ under each of the OS, US, and NS.

FIG. 6 shows the result of the analysis of variance on a 5% significant level performed by using the calculated RMS values. In FIG. 6, each of "<" and ">" represents the magnitude relationship between a comparison pair having a statistically significant difference therebetween.

By the result shown in FIG. 6, it was proved that the RMS value under the NS was smaller than the RMS value under the OS in each of the regions $L_1$, $L_3$, and $L_7$, the RMS value under the NS was smaller than the RMS value under the US in each of the regions $L_1$, $L_4$, and $L_7$, and the RMS value under the US was smaller than the RMS value under the OS in each of the regions $L_3$ and $L_6$.

This has proved that the RMS value of the synchronous contraction waveform under the NS is smaller than the RMS values under the US and the OS in each of the regions (regions $L_1$, $L_3$, $L_4$, and $L_7$) where the RMS value under the NS has statistically significant differences between itself and the RMS values under the US and the OS and that the RMS value under the US is smaller than the RMS value under the OS in each of the regions ($L_3$ and $L_6$) where the RMS values under the US and the OS has statistically significant differences therebetween.

The result of the analysis of variance corresponds to the above-mentioned subjective judgement of the degree of comfort of wheel steering by the driver.

Accordingly, it will be understood that the use of the intensity information of the synchronous contraction waveform allows proper evaluation of the degree of comfort of the wheel steering.

It can therefore be said that the use of frequency information contained in a specified intensity range in the synchronous contraction waveform allows proper evaluation of the degree of comfort of wheel steering.

Since the RMS values vary with time, as shown in FIG. 5, the calculation of RMS values at specified time intervals further allows the evaluation of the degree of comfort which varies with time. For example, even under the NS which is the best in the degree of comfort among the US, the OS, and the NS, a region in which the RMS value increases and the degree of comfort deteriorates can be determined. This helps the development of a vehicle and a tire which investigate wheel steering comfort.

Although the above-mentioned example has described the case where the degree of comfort is evaluated when a driver drives a vehicle and steers a wheel, the present invention does not limit the evaluation target of the degree of comfort to the steering of a wheel. The evaluation target may be any work activity provided that it is performed antagonistically by a pair of left and right muscles provided in a human body in bilaterally symmetrical relation.

Although the apparatus and method of evaluating a degree of work comfort according to the present invention have been described in detail, the present invention is not limited to the embodiment described above. It will be appreciated that various changes and modifications can be made in the invention without departing from the gist thereof.

INDUSTRIAL APPLICABILITY

As described above, the present invention measures myoelectric potentials during a work activity which is performed antagonistically by a pair of left and right muscles provided in a human body in bilaterally symmetrical relation, generates a synchronous contraction waveform from the pair of muscles, and evaluates the level of the degree of work comfort from the intensity information or frequency information of the generated synchronous contraction waveform. This allows the evaluation of the degree of comfort of a work activity from the result of short-period measurement without imposing a restriction on, e.g., the breathing of an activity worker as has been imposed conventionally.

The invention claimed is:

1. An apparatus for evaluating a degree of work comfort by measuring myoelectric potentials during a work activity which is performed antagonistically by a pair of left and right muscles provided in a human body in bilaterally symmetrical relation, the apparatus comprising:

a pair of detection sensors for detecting the myoelectric potentials of the pair of left and right muscles provided in the human body in bilaterally symmetrical relation, the myoelectric potentials produced by actions of the pair of the muscles of the human body during the work activity;

an amplifier for amplifying the pair of myoelectric potentials detected by the detection sensors;

a waveform processing unit for generating a synchronous contraction waveform of the pair of muscles from time-series waveforms of the pair of amplified myoelectric potentials; and an evaluation unit for evaluating a level of the degree of comfort of the work activity based on intensity information of the generated synchronous contraction waveform or frequency information of the generated synchronous contraction waveform contained in a specified intensity range, wherein the waveform processing unit is configured to perform full-wave rectification with respect to the time-series waveforms of the pair of myoelectric potentials and select, as a signal value of the synchronous contraction waveform, a smaller value from two respective values at a given time in the time-series waveforms of the pair of myoelectric potentials that have been subjected to the full-wave rectification, thereby generating the synchronous contraction waveform.

2. The apparatus for evaluating a degree of work comfort according to claim 1, wherein the evaluation unit is configured to calculates the intensity information of the generated synchronous contraction waveform or the frequency information of the generated synchronous contraction waveform at specified time intervals and evaluate the level of the degree of comfort of the work activity at the specified time intervals based on results of the calculation.

3. The apparatus for evaluating a degree of work comfort according to claim 1 or 2, wherein the waveform processing unit is configured to perform a normalizing process with respect to the time-series waveforms of the pair of amplified myoelectric potentials by using a maximum myoelectric potential and generate the synchronous contraction waveform by using the time-series waveforms that have been subjected to the process.

4. The apparatus for evaluating a degree of work comfort according to claim 1 or 2, wherein the work activity comprises steering of a wheel in driving a vehicle.

5. The apparatus for evaluating a degree of work comfort according to claim 1 or 2, wherein the pair of muscles comprise deltoid muscles positioned in shoulders of the human body.

6. An apparatus for evaluating a degree of work comfort by measuring myoelectric potentials during a work activity which is performed antagonistically by a pair of left and right muscles provided in a human body in bilaterally symmetrical relation, the apparatus comprising:
   a pair of detection sensors for detecting the myoelectric potentials of the pair of left and right muscles provided in the human body in bilaterally symmetrical relation, the myoelectric potentials produced by actions of the pair of the muscles of the human body during the work activity;
   an amplifier for amplifying the pair of myoelectric potentials detected by the detection sensors;
   a waveform processing unit for generating a synchronous contraction waveform of the pair of muscles from time-series waveforms of the pair of amplified myoelectric potentials; and
   an evaluation unit for evaluating a level of the degree of comfort of the work activity based on intensity information of the generated synchronous contraction waveform or frequency information of the generated synchronous contraction waveform contained in a specified intensity range,
   wherein the waveform processing unit is configured to perform full-wave rectification with respect to the time-series waveforms of the pair of myoelectric potentials and calculate, as a signal value of the synchronous contraction waveform, a geometric mean value of two respective signal values at a given time in the time-series waveforms of the pair of myoelectric potentials that have been subjected to the full-wave rectification, thereby generating the synchronous contraction wave form.

7. The apparatus for evaluating a degree of work comfort according to claim 6, wherein the evaluation unit is configured to calculate the intensity information of the generated synchronous contraction waveform or the frequency information of the generated synchronous contraction waveform at specified time intervals and evaluate the level of the degree of comfort of the work activity at the specified time intervals based on results of the calculation.

8. The apparatus for evaluating a degree of work comfort according to claim 6 or 7, wherein the work activity comprises steering of a wheel in driving a vehicle.

9. The apparatus for evaluating a degree of work comfort according to claim 6 or 7, wherein the pair of work muscles comprise deltoid muscles positioned in shoulders of the human body.

10. A method of evaluating a degree of work comfort by measuring myoelectric potentials during a work activity which is performed antagonistically by a pair of left and right muscles provided in a human body in bilaterally symmetrical relation, the method comprising:
    detecting the myoelectric potentials of the pair of left and right muscles provided in the human body in bilaterally symmetrical relation, the myoelectric potentials produced by actions of the pair of the muscles of the human body during the work activity;
    amplifying the pair of myoelectric potentials;
    generating a synchronous contraction waveform of the pair of muscles from time-series waveforms of the pair of amplified myoelectric potentials; and
    evaluating a level of the degree of comfort of the work activity based on intensity information of the generated synchronous contraction waveform or frequency information of the generated synchronous contraction waveform of the generated synchronous contraction waveform contained in a specified intensity range,
    wherein generating the synchronous contraction waveform includes performing full-wave rectification with respect to the time-series waveforms of the pair of myoelectric potentials and selecting, as a signal value of the synchronous contraction waveform, a smaller value from two respective values at a given time in the time-series waveforms of the pair of myoelectric potentials that have been subjected to the full-wave rectification.

11. The method of evaluating a degree of work comfort according to claim 10, wherein evaluating the level of the degree of comfort of the work activity includes calculating the intensity information or the frequency information of the generated synchronous contraction waveform at specified time intervals and evaluating the level of the degree of comfort of the work activity at the specified time intervals based on results of the calculation.

12. The method of evaluating a degree of work comfort according to claim 10 or 11, wherein, in generating the synchronous contraction waveform, a waveform processing unit performs a normalizing process with respect to the time-series waveforms of the pair of amplified myoelectric potentials by using a maximum myoelectric potential and generates the synchronous contraction waveform by using the time-series waveforms that have been subjected to the process.

13. The method of evaluating a degree of work comfort according to claim 10 or 11, wherein the work activity comprises steering of a wheel in driving a vehicle.

14. The method of evaluating a degree of work comfort according to claim 10 or 11, wherein the pair of muscles comprise deltoid muscles positioned in shoulders of the human body.

15. A method of evaluating a degree of work comfort by measuring myoelectric potentials during a work activity which is performed antagonistically by a pair of left and right muscles provided in a human body in bilaterally symmetrical relation, the method comprising:
    detecting the myoelectric potentials of the pair of left and right muscles provided in the human body in bilaterally symmetrical relation, the myoelectric potentials produced by actions of the pair of the muscles of the human body during the work activity;

amplifying the pair of myoelectric potentials;

a step of generating a synchronous contraction waveform of the pair of muscles from time-series waveforms of the pair of amplified myoelectric potentials; and evaluating a level of the degree of comfort of the work activity based on intensity information of the generated synchronous contraction waveform or frequency information of the generated synchronous contraction waveform of the generated synchronous contraction waveform contained in a specified intensity range, wherein generating the synchronous contraction waveform includes performing full-wave rectification with respect to the time-series waveforms of the pair of myoelectric potentials and calculating, as a signal value of the synchronous contraction waveform, a geometric mean value of two respective signal values at a given time in the time-series waveforms of the pair of myoelectric potentials that have been subjected to the full-wave rectification.

16. The method of evaluating a degree of work comfort according to claim 15, wherein, evaluating the level of the degree of comfort of the work activity includes calculating the intensity information or the frequency information of the generated synchronous contraction waveform at specified time intervals and evaluating the level of the degree of comfort of the work activity at the specified time intervals based on results of the calculation.

17. The method of evaluating a degree of work comfort according to claim 15 or 16, wherein the work activity comprises steering of a wheel in driving a vehicle.

18. The method of evaluating a degree of work comfort according to claim 15 or 16, wherein the pair of muscles comprise deltoid muscles positioned in shoulder of the human body.

* * * * *